United States Patent [19]

Jenkins

[11] Patent Number: 5,027,643
[45] Date of Patent: Jul. 2, 1991

[54] METHOD AND APPARATUS FOR DETECTING LOW VOLATILITY ATMOSPHERIC VAPORS

[75] Inventor: Anthony Jenkins, North Reading, Mass.

[73] Assignee: Ion Track Instruments, Inc., Burlington, Mass.

[21] Appl. No.: 503,698

[22] Filed: Apr. 3, 1990

[30] Foreign Application Priority Data

Mar. 24, 1990 [GB] United Kingdom ............... 9006658

[51] Int. Cl.⁵ ...................... G01N 30/86; G01N 33/22
[52] U.S. Cl. ...................................... 73/23.39; 422/89
[58] Field of Search ............... 73/23.39, 23.41, 31.07; 422/89; 436/161, 178

[56] References Cited

U.S. PATENT DOCUMENTS 3,568,411 3/1971 Dravnicks et al. ............ 73/23.39 X
4,116,042 9/1978 Jenkins et al. ..................... 73/23.39

Primary Examiner—Hezron E. Williams
Assistant Examiner—Joseph W. Roskos
Attorney, Agent, or Firm—Anthony J. Casella; Gerald E. Hespos

[57] ABSTRACT

An apparatus and method is provided for detecting terrorist bombs. The apparatus is operative to detect small amounts of low volatility atmospheric vapors which are emitted into the surrounding air from the bomb. The apparatus includes a heated inlet nozzle which delivers the air to a silicone membrane. A pair of identical capillaries are disposed downstream from the membrane, with one capillary being polarized, and the other being non-polarized. The heating of the inlet nozzle is periodically increased rapidly to cause extremely low volatility explosive vapors to evaporate and diffuse through the membrane. Detectors disposed downstream from the capillaries detect the presence of the vapors impinging thereon. Differences in the signals generated by the two detectors is indicative of the presence of an explosive. A microprocessor is provided to recalibrate the detectors after each heating cycle.

17 Claims, 2 Drawing Sheets

METHOD AND APPARATUS FOR DETECTING LOW VOLATILITY ATMOSPHERIC VAPORS

FIELD OF THE INVENTION

This invention relates to a method and apparatus for detecting explosive vapors and to bomb detectors employing the method and apparatus.

BACKGROUND OF THE INvENTION

The prior art includes detectors for selectively detecting explosive vapors such as dynamite and tri-nitrotoluene (TNT) in the atmosphere. One effective prior art detector is disclosed in U.S. Pat. No. 4,116,042, which issued to Anthony Jenkins on Sept. 26, 1978 and shows a system for continuously detecting explosive vapors which gave a rapid response in less than one second of sampling the vapor. As shown schematically in FIG. 1, air was drawn into this prior art detector through a heated nozzle 21 by the action of a small suction pump 30. The hot air flow was caused to impinge onto a heated elastomeric membrane 22 made of di-methyl silicone rubber. The membrane 22 was chosen because of a favorable property which allows low volatility vapors to diffuse through the membrane while blocking the transport of unwanted gases such as oxygen. Explosive vapors were transmitted in this prior art detector with an efficiency of about 2%.

Explosive vapors which were transmitted through the membrane 22 in the prior art apparatus of U.S. Pat. No. 4,116,042 were carried on an inert carrier gas stream and split into two flow paths. The two flows were passed down two, short open tubular chromatographic capillary columns 25 and 26 toward detectors 27 and 28 respectively. The capillary column 26 was coated with a polar chromatographic liquid, while the capillary column 25 either remained uncoated or was coated with non-polar material. The flows in the prior art device of U.S. Pat. No. 4,116,042 were arranged such that common interfering compounds, such as chlorinated solvents, travelled down the two columns 25,26 and arrived at detectors 28 through the polar column 26 a few milli-seconds before arriving at the detector 27 down the non-polar column 26. Explosive vapors are mostly very polar and are absorbed strongly down the polar column where they are delayed. The explosive vapor peak arrived at the detector through the non-polar column 25 before the polar detector 28.

The signals of the two detectors 27 and 28 in the prior art detector were processed, and the difference between the two signals was computed in an analogue summing amplifier. The difference signals generated in the prior art detector for explosive and non-explosive vapors are shown in FIGS. 2a and 2b. It can be seen that the difference signal for explosives responds in the opposite direction to non-explosives. A logic gating circuit was arranged in the prior art detector to allow the signals to be presented at an output device such as an audible alarm or visual readout when the difference signal went negative while the signal strength was increasing.

The prior art system shown in FIG. 1 and described in greater detail in U.S. Pat. No. 4,116,042 provides excellent sensitivity and selectivity to most explosives. Unfortunately, small amounts of explosive vapor in the presence of halogenated materials cannot be detected in this prior art device because the difference signal for halogens overpowers the difference signal for explosives. A further limitation of the prior art device is that although the electron capture detector itself may be sensitive to one or two parts of explosive vapors in one trillion ($10^{12}$) parts of pure carrier gas, the concentration gradient developed across the membrane reduces this detection limit by a factor of 10 or more. Furthermore, the impurity "noise" in the atmosphere causes fluctuation in the concentration of responding vapors reaching the detector in the prior art device. This increases noise levels also by a factor of ten. The net effect is that the limit of detection of the prior art device is one part of explosive vapor in $10^{10}$ parts of air. This is insufficient to detect the vapors from the "plastic" explosives largely comprised of cyclotrimethylenetrinitramine (otherwise known as RDX), and pentaerythritol tetranitrate (PETN). A sensitivity to one part of RDX in $10^{12}$ parts of air is required to provide a means of detection for the plastic explosives.

In other known devices, air samples are collected in a trap before being desorbed into a sensitive detector such as an electron capture detector (ECD). Unfortunately, several materials commonly present in the atmosphere respond on the ECD and have to be separated from the explosive vapor in a chromatograph separation process. If the vapors from dynamite, TNT and plastic explosives are sought by this technique, then several minutes are required to separate these compounds from the other, mostly volatile, interfering compounds in the atmosphere. One further major disadvantage with this technique is that sampling valves are normally deployed to control the sampling and desorption processes. These present large surface areas for irreversible adsorption of the very low volatility explosive vapors. Most, if not all, of the vapors from RDX and PETN are lost in the system and are never detected. No such detector has been successfully developed to detect these vapors in the quantities necessary to achieve detection of terrorist bombs made from plastic explosives.

SUMMARY OF THE INVENTION

The apparatus of the subject invention is a further improvement of the explosive detector described in U.S. Pat. No. 4,116,042, and shown schematically in FIG. 1. More particularly, the subject invention is directed to a method and apparatus which will rapidly detect the vapors of all explosives including RDX and PETN. This has been achieved by a novel trapping system which has no moving parts, has extremely low volume and no metallic surfaces in the separation system. The system of the subject invention is capable of detecting dynamite and di nitro toluene (a component of commercial TNT), in less than 1 second and the plastic explosives in 10 to 20 seconds.

DETAILED DESCRIPTION OF THE PREFERRED EMBODIMENT

Figure 1:
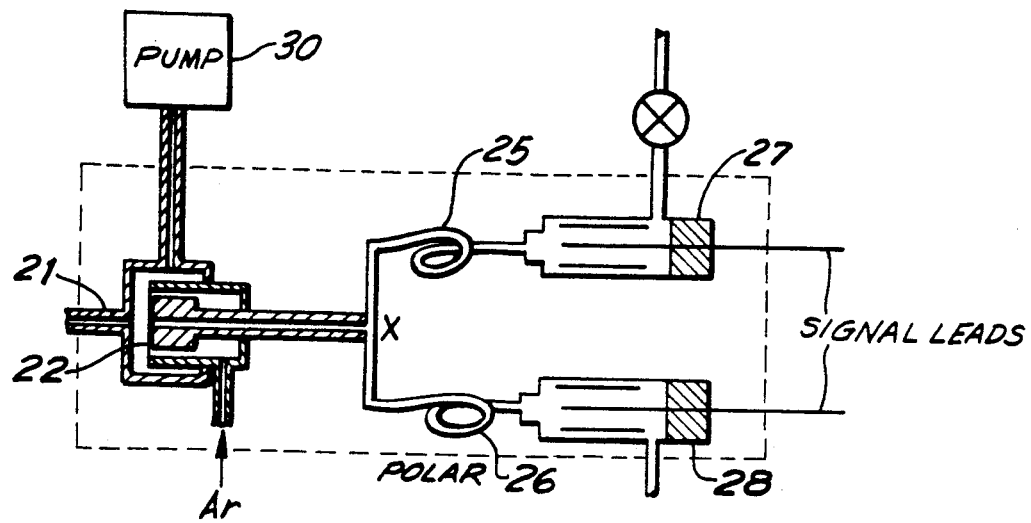
FIG. 1 is a schematic cross-sectional view of a prior art apparatus for detecting vapors of explosives.
Figure 2A:
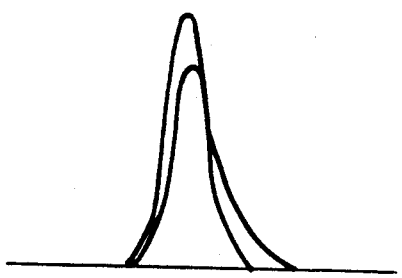
FIG. 2a is a graph showing responses of the prior art detector to halogenated materials.
Figure 2B:
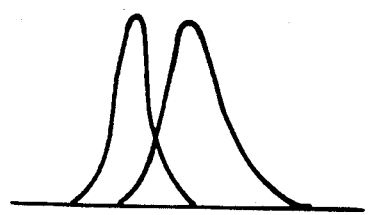
FIG. 2b is a graph showing the response of the prior art detector to explosives.
Figure 3:
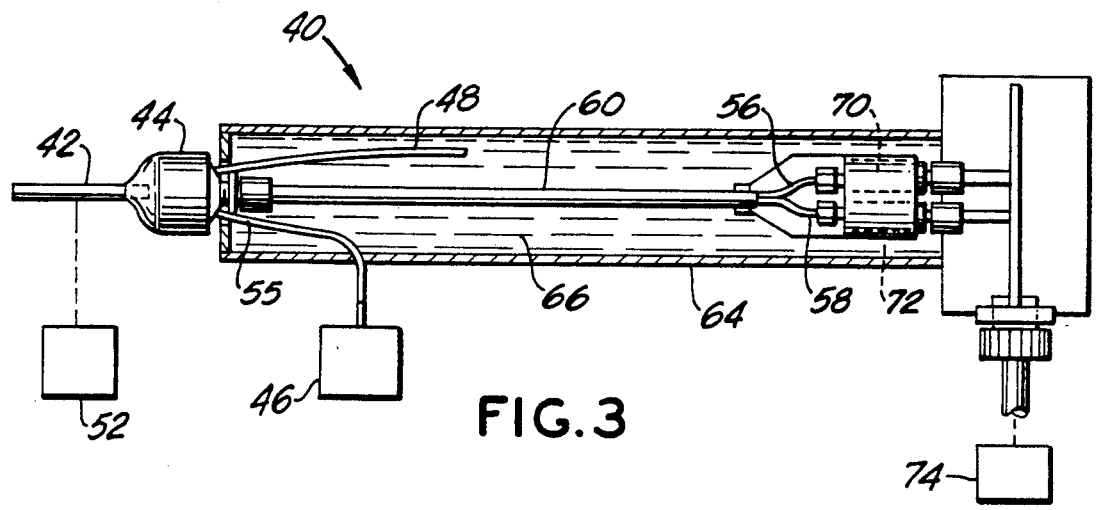
FIG. 3 is a schematic cross-sectional view of the detector of the subject invention.
Figure 4:
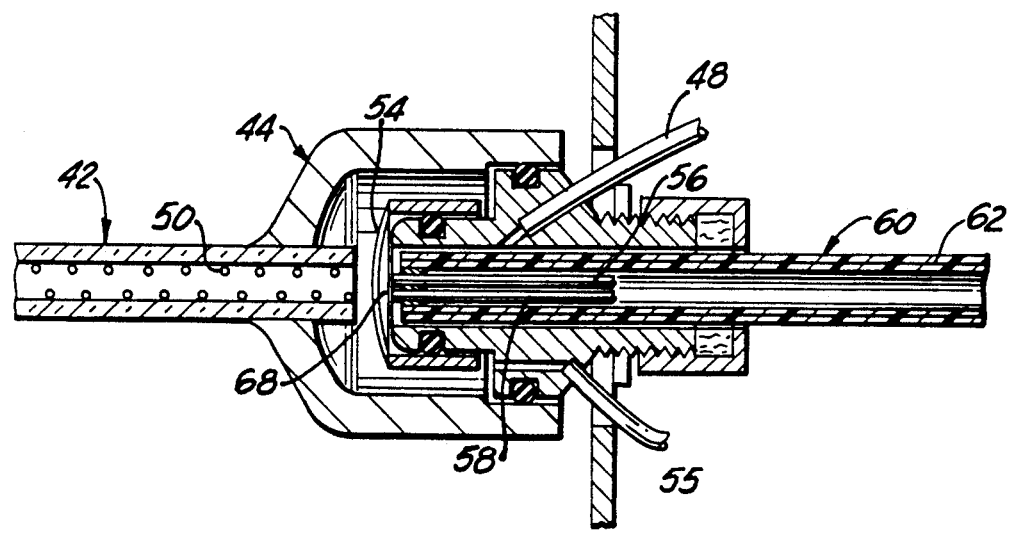
FIG. 4 is a cross-sectional view of the nozzle and membrane mount of the detector of the subject invention.

The apparatus of the subject invention is identified generally by the numeral 40 in FIG. 3. The apparatus 40 includes an inlet nozzle 42 into which sampled air being analyzed for the presence of explosive vapors is drawn and a membrane housing 44 into which the sampled air is directed by the inlet nozzle 42. The inlet nozzle 42 and the membrane housing 44 are shown in greater detail in FIG. 4.

Generally, during operation of the apparatus 40, air is drawn into the inlet nozzle 42 from the vicinity of a suspect object or package which is being inspected for possible terrorist explosive devices. The air flow through the inlet nozzle 42 is generated by a suction pump 46 which draws both the sampled air and an inert carrier gas, such as argon from a source 48 into the membrane housing 44. The inlet nozzle 42 preferably is made of all glass construction with thin walls which have a low thermal inertia.

A coil of platinum wire 50 is held inside the full length of the glass inlet nozzle 42 and serves as a heater to warm the sampled air stream. An electric current is passed through the platinum wire coil 50, and the resistance of the wire 50 is measured by ohmmeter 52 to provide a measure of the temperature. The temperature of the inlet nozzle 42 is, by this means, controlled to a level which will allow the passage of most explosive vapors without adsorption in the walls of the inlet nozzle 42. The length of the inlet nozzle 42 is selected so that all of the sampled air reaches the temperature of the platinum wire coil 50 before striking the dimethyl silicone membrane 54 shown in FIG. 4. The sampled air is then drawn down the exhaust line 55 to a suction pump 46.

The flow of air impinging on the membrane 54 maintains the membrane near to the temperature of the warm air. This temperature is sufficient to allow the diffusion through the membrane 54 of dynamite and the more volatile impurity materials in the other explosives. Most interfering atmospheric contaminants are more volatile than dynamite and will also pass directly through the membrane at this temperature. The vapors of TNT, RDX, and PETN are all trapped on the surface of the membrane 54 at this temperature and do not pass through the membrane 54 into the carrier gas stream.

The vapors which do pass through the membrane 54 are swept by the carrier gas directly into two pure quartz chromatographic capillary columns 56 and 58. The capillary columns 56 and 58 are supported in an elongated heater jacket 60 defined by a Teflon ® tube with a heater wire 62 in its wall. The heater jacket 60, in turn, is mounted in a housing 64 having a thermal insulation 66 between the heater jacket 60 and the housing 64. The capillary column 56 is coated with a polar chromatographic liquid, while the capillary column 58 is coated with a non-polar material. A dead volume 68 exists between the membrane 54 and the columns 56 and 58 and is kept extremely small, preferably below 50 micro liters and most preferably on the order of ten micro liters. This small size of the dead volume 68 improves resolution of elution times between different compounds and enables very fast analyses to be performed. The capillary columns 56 and 58 are maintained at a temperature between 150° C and 190° C which is much higher than previously used in the prior art described in U.S. Pat. No. 4,116,042. At these temperatures, most materials travel down the non-polar column 58 at the speed of the carrier gas, i.e., they suffer no delay in the liquid coating in the wall of the capillary column 58. Most materials also travel down the polar capillary column 56 at the speed of the carrier gas. The geometry of the two columns 56 and 58 is kept identical so that these materials arrive at the detectors 70 and 72 simultaneously, and therefore respond simultaneously. If both detectors 70 and 72 have the same sensitivity, then no difference between the two detector responses is observed. This is true for all weak absorbers, such as oxygen, and all commonly occurring halogenated materials, such as refrigerants and solvents.

When an explosive vapor, such as nitro-glycine or ethylene glycol di-nitrate, passes down the columns, the explosive, being either polar or low volatility, is delayed down the polar column 56. The non-polar detector 62 responds before the detector 60 from the polar column 56 just as was described in the prior art detector disclosed in U.S. Pat. No. 4,116,042. The major difference is that now explosives can be detected in halogenated backgrounds and no false "halogen" alarm is made. Also, the impurity noise in the two detectors is identical and cancels in the difference measurement.

After a short period of sampling the atmosphere, any extremely low volatility explosives vapors such as RDX, PETN, or TNT which may be present, accumulate on the membrane 54. Increased heating is applied to the inlet nozzle 42 periodically (e.g. every 10–20 seconds) so that the temperature is rapidly increased from a first temperature between ambient and about 90° C to a second temperature of between about 150° C and 220° C. At this second temperature, any explosive which has been deposited either in the nozzle 42 or on the membrane 54, is quickly evaporated and diffuses through the membrane 54 into the carrier gas stream. A high temperature is required to allow rapid diffusion to produce a sharp "peak" of vapor. Some explosives break down rapidly above 200° C, and so it is essential to maintain good control of the desorption temperature. This is again preferably achieved by using the platinum wire coil 50 as both the heater and thermometer in a closed loop temperature control system.

The desorbed explosive travels down the two columns 56 and 58 and is delayed in the polar column 56 as in the prior art apparatus identified above. This causes a difference signal from the two detectors 70 and 72 which is used to signal the presence of explosives.

Unfortunately, every time the membrane 54 is heated, the dynamic capacity and diffusion co-efficient of the membrane 54 for other interfering volatile impurities changes. This results in a response in each detector 70 and 72 at every heating cycle. The response can be completely balanced if the elution time or phase of the responses is identical and the sensitivity of the detectors 70 and 72 is identical. This ideal situation does not occur in practice. In particular, the sensitivity of detectors 70 and 72 may differ slightly and the phase of the two responses may also differ. Different diameters of the columns 56 and 58 or coating thicknesses thereon and temperature differentials between columns 56 and 58 may cause the elution time to differ. The subject apparatus 40, however, is uniquely adapted to maintain the phase and the responses identical for normal air background by a novel method and means for analyzing the signals.

The similar signals containing random fluctuations are difficult to match in phase, but the time difference of the signal produced in each desorption cycle can be easily determined. The phase difference is first measured during a cycle in which normal background air is sampled. This is achieved by digitizing the signal in a micro processor system 74 and measuring the time to first respond after heating the membrane 54. This time difference can be checked in every cycle during which no response is obtained.

A difference signal is then digitally computed after allowing for the phase shift between the two signals. The gain of one of the signals is adjusted automatically until no difference signal remains after adjusting for both phase and gain, i.e., $g = S_1(t)/S_2(t+dt)$. A weighted mean gain calibration factor is calculated every cycle in which no response is obtained. The difference signal D is calculated in an algorithm:

$$D = S_1(t) - gS_1(t+dt)$$

where
$S_1(t)$ is the signal at time t from detector 1

$S_2(t+dt)$ is the signal at time $t+dt$ from detector 2
dt is the phase shift between the signals
g is the gain factor computed from previous cycles.

The algorithm compensates for volatile impurity changes in the atmosphere and eliminates the noise in the difference signal due to such impurities.

The apparatus and method described herein achieves several significant improvements to the sensitivity and selectivity. In particular, a greater concentration gain between atmosphere and the carrier gas is achieved due to the unrestricted path of sampled air and the extremely low volume of the desorption chamber. This allows a high air flow, F, at the same time as an extremely low carrier flow, f, and still provides extremely fast responses.

The concentration gain, C is deduced from:

$$c = \frac{c_o}{c_i} = \frac{F}{f} \cdot \frac{T_s}{T_p} \cdot e.$$

where
$C_o$ is the concentration reaching the detector;
$C_i$ is the concentration in the sampled air;
$T_s$ is the sampling time of the sampled air; and,
$T_p$ is the peak width at half height of the desorbed peak;
e in the trapping efficiency.

$T_s$ can be chosen from 2 seconds to a few minutes, but in practice, sufficient sensitivity is achieved after 10 to 20 seconds.

$T_p$ is adversely affected by the volume in the gas paths after the membrane and is also dependent on the rate of temperature rise in the membrane itself. Both of these points have been addressed in the design illustrated in FIGS. 3 and 4 to reduce $T_p$ to below 1 second.

The ratio F/f can be in the region from 10 to 1000. At higher sample flow, F, the trapping efficiency is reduced and a high flow may cause dilution of the finite volume of vapor which is available. In practice, little or no concentration increase is gained beyond a flow ratio of 100.

The apparatus 40 also achieves a much lower noise level which has resulted in the detection of much smaller quantities of explosive vapors. Furthermore, the apparatus 40 enables a reduction of interfering responses by cancellation in the dual detection system and ease of operation due to the automatic calibration of both gain and phase difference in the signal processing circuits of the processor 74 and the methods defined by the preceding algorithms. The combined effects of the apparatus 40 have led to the development of an apparatus capable of detecting the vapors from the most involatile of the plastic explosives used in terrorist bombs.

I claim;

1. An apparatus for detecting the presence of at least one selected constituent in a selected sample of air, said apparatus comprising:
    nozzle means for receiving air from the sample;
    suction means for creating a flow of the air through the nozzle means;
    heating means for heating the flow of air in the nozzle means;
    means for changing the temperature to which the air in the nozzle means is heated;
    membrane means in proximity to said nozzle means for receiving at least the selected constituents in the air flowing through the nozzle means;
    first and second chromatographic capillaries in proximity to the membrane means for receiving the constituents diffused through the membrane means, said capillaries being of substantially identical dimensions, said first capillary being internally coated with a layer of material which selectively delays the elution of the constituent;
    first and second detectors in communication with the respective first and second capillaries for generating signals in response to gases impinging thereon; and
    signal processing means operatively connected to the detectors for identifying differences in phase of the signals detected by the first and second detectors respectively, whereby a difference in phase between selected signals generated by said first and second detectors respectively is indicative of the presence of the constituent gas.

2. An apparatus as in claim 1 wherein the heating means comprises a platinum wire.

3. An apparatus as in claim 1 wherein the nozzle is formed from a thin walled glass tube, and wherein the heating means comprises a platinum coil disposed in the nozzle, said heating means further comprising means for measuring the resistance in the platinum coil and means for altering the electric current therein, the electric current being varied and the resistance being measured for controlling the temperature of the platinum coil and for thereby controlling the temperature of the air.

4. An apparatus as in claim 3 wherein the heating means is operative to rapidly raise the temperature of air in the nozzle from a first temperature of between ambient temperature and about 90° C to a second temperature of between about 150° C to 220° C.

5. An apparatus as in claim 1 further comprising a second heating means for maintaining a temperature of the capillaries between 150° C and 190° C.

6. An apparatus as in claim 1 further defining a chamber intermediate the membrane and the capillaries, the chamber defining a volume of less than approximately 50 micro liters.

7. An apparatus as in claim 1 wherein the membrane is formed from a dimethyl silicone.

8. An apparatus as in claim 1 wherein the chromatographic capillaries are formed from silica.

9. An apparatus as in claim 1 further comprising means for maintaining the responses of the detectors identical at all times to commonly occurring atmospheric contaminants.

10. An apparatus as in claim 9 wherein the means for maintaining the response of the detectors identical comprises means for calculating a difference signal D between the two detectors as $$S_1(t) - gS_2(t+dt)$$

where $S_1$ (t) is a signal at time t from the first detector; $S_2$ (t+dt) is a signal at time (t+dt) from the second detector; dt is a phase shift between signals as determined by the signal processing means, and g is a gain factor computed from previous analyses.

11. A method for identifying the presence of a selected constituent in a flow of air, said method comprising the steps of:
 generating a flow of said air;
 heating the air in said flow;
 providing a dimethyl silicone membrane in said flow for blocking selected unwanted constituents in said flow and permitting at least the selected constituent to diffuse through the membrane;
 periodically raising the temperature of the air directed toward the membrane;
 directing the air diffused through said membrane into first and second dimensionally identical capillaries, said first capillary being coated internally with a layer of material which selectively delays the elution of the constituent;
 generating signals for detecting the presence of materials passing through the capillaries;
 identifying phase differences existing at times when said constituents are known not to be present to identify a difference signal D;
 adjusting the generated signals by the amount of the difference signal D; and
 identifying actual phase differences for the adjusted signals to identify the presence of said constituent.

12. A method as in claim 11 wherein the temperature of the air directed toward the membrane is periodically raised from a first temperature between ambient and about 90° C. to a second temperature between 150° C. and 220° C.

13. A method as in claim 12 further comprising the step of continuously measuring and adjusting the temperature of the air directed toward the membrane for maintaining the air at selected temperatures.

14. A method as in claim 11 wherein the difference signal is calculated by $$S_1(t) - gS_2(t+dt)$$

where: $S_1(t)$ is the signal at time t from the first detector; $S_2(t+dt)$ is the signal at time t+dt from the second detector; dt is a phase shift between signals; and g is a gain factor computed from previous analyses.

15. An apparatus for detecting the presence of at least one selected constituent in a selected sample of air, said apparatus comprising:
 nozzle means for receiving air from the sample, the nozzle means being formed from a thin walled glass tube;
 suction means for creating a flow of the air through the nozzle means;
 heating means for heating the flow of air in the nozzle means, the heating means comprises a platinum coil disposed in the nozzle, said heating means further comprising means for measuring the resistance in the platinum coil means for altering the electric current therein, the electric current being varied and the resistance being measured for controlling the temperature of the platinum coil and for thereby controlling the temperature of the air;
 membrane means in proximity to said nozzle means for receiving at least the selected constituents in the air flowing through the nozzle means;
 first and second chromatographic capillaries in proximity to the membrane means, said capillaries being of substantially identical dimensions, said first capillary being internally coated with a layer of material which selectively delays the elution of the constituent;
 first and second detectors in communication with the respective first and second capillaries for generating signals in response to gases impinging thereon; and
 signal processing means operatively connected to the detectors for identifying differences in phase of the signals detected by the first and second detectors respectively, whereby a difference in phase between selected signals generated by said first and second detectors respectively is indicative of the presence of the constituent gas.

16. An apparatus as in claim 15 wherein the heating means is operative to rapidly raise the temperature of air in the nozzle means from a first temperature of between ambient temperature and about 90° C. to a second temperature of between about 150° C. to 220° C.

17. An apparatus for detecting the presence of at least one selected constituent in a selected sample of air, said apparatus comprising:
 nozzle means for receiving air from the sample;
 suction means for creating a flow of the air through the nozzle means;
 heating means for heating the flow of air in the nozzle means;
 membrane means in proximity to said nozzle for receiving at least the selected constituents in the air flowing through the nozzle means;
 first and second chromatographic capillaries in proximity to the membrane means for receiving the contituents diffused through the membrane means, said capillaries being of substantially identical dimensions, said first capillary being internally coated with layer of material which selectively delays the elution of the constituent;
 second heating means for maintaining a temperature of the capillaries between 150° C. and 190° C.;
 first and second detectors in communication with the respective first and second capillaries for generating signals in response to gases impinging thereon; and
 signal processing means operatively connected to the detectors for identifying differences in phase of the signals detected by the first and second detectors respectively, whereby a difference in phase between selected signals generated by said first and second detectors respectively is indicative of the presence of the constituent gas.

* * * * *